(12) United States Patent
Ayame et al.

(10) Patent No.: US 7,729,751 B2
(45) Date of Patent: Jun. 1, 2010

(54) ELECTRONIC ENDOSCOPIC APPARATUS

(75) Inventors: Daisuke Ayame, Saitama (JP); Shinji Takeuchi, Saitama (JP)

(73) Assignee: Fujinon Corporation, Saitama-Ken (JP)

( * ) Notice: Subject to any disclaimer, the term of this patent is extended or adjusted under 35 U.S.C. 154(b) by 916 days.

(21) Appl. No.: 11/528,537

(22) Filed: Sep. 28, 2006

(65) Prior Publication Data
US 2007/0078299 A1  Apr. 5, 2007

(30) Foreign Application Priority Data
Sep. 30, 2005  (JP)  ............................. 2005-289145

(51) Int. Cl.
*A61B 6/00* (2006.01)
(52) U.S. Cl. .................... 600/477; 600/476; 600/478
(58) Field of Classification Search .................. 600/101, 600/160, 476–478; 362/572, 574
See application file for complete search history.

(56) References Cited

U.S. PATENT DOCUMENTS

| | | | |
|---|---|---|---|
| 5,187,572 A | 2/1993 | Nakamura et al. | |
| 6,464,633 B1 | 10/2002 | Hosoda et al. | |
| 7,393,321 B2 * | 7/2008 | Doguchi et al. | ............ 600/109 |
| 2003/0001104 A1 * | 1/2003 | Sendai et al. | ............ 250/458.1 |
| 2004/0122291 A1 | 6/2004 | Takahashi | |
| 2007/0153542 A1 * | 7/2007 | Gono et al. | ................. 362/574 |

FOREIGN PATENT DOCUMENTS

| | | |
|---|---|---|
| EP | 1 079 255 A2 | 2/2001 |
| JP | 2002-238846 A | 8/2002 |
| JP | 2003-93336 A | 4/2003 |
| WO | WO-2005/031436 A1 | 4/2005 |

OTHER PUBLICATIONS

Miyake, Analysis and Evaluation of Digital Color Image, University Tokyo Press, pp. 148-153.

* cited by examiner

*Primary Examiner*—Long V Le
*Assistant Examiner*—Jacqueline Cheng
(74) *Attorney, Agent, or Firm*—Birch, Stewart, Kolasch & Birch, LLP

(57) ABSTRACT

A spectral image obtainment unit obtains spectral image data by receiving reflection light in different wavelength bands, into which light reflected by a living body mucous membrane has been separated, at a light receiving unit by causing a ratio of a light receiving level in a short wavelength band with respect to a light receiving level in a long wavelength band to be greater than a ratio of spectral reflectance in the short wavelength band at the living body mucous membrane with respect to spectral reflectance in the long wavelength band thereat. A spectral image data operation unit performs a spectral image estimation operation by correcting the value of the spectral image data to that of spectral image data obtained by receiving light without causing the ratio to increase. Accordingly, a diagnostic spectral image of the living body mucous membrane is obtained in an electronic endoscopic apparatus.

16 Claims, 7 Drawing Sheets

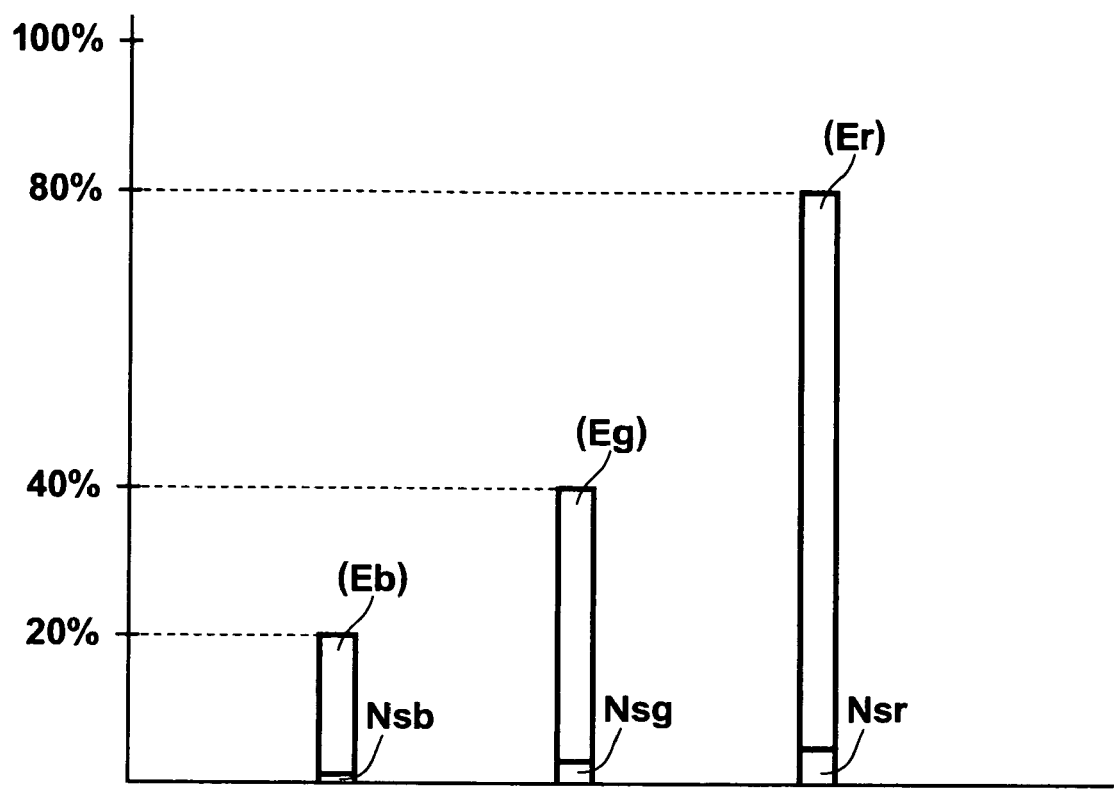

US 7,729,751 B2

ELECTRONIC ENDOSCOPIC APPARATUS

BACKGROUND OF THE INVENTION

1. Field of the Invention

The present invention relates to an electronic endoscopic apparatus. Particularly, the present invention relates to an electronic endoscopic apparatus for diagnosing a living body mucous membrane by producing a spectral image of the living body mucous membrane.

2. Description of the Related Art

Conventionally, an electronic endoscopic apparatus (Narrow Band Imaging-NB1) that produces a spectral image for diagnosis is well known as an electronic endoscopic apparatus using a solid-state imaging device. In the electronic endoscopic apparatus (Narrow Band Imaging-NB1), narrow-band spectral images of a living body mucous membrane of the digestive organ, such as the stomach, are obtained by imaging the living body mucous membrane through a narrow-band-pass filter, which transmits light only in a narrow wavelength band. Then, the narrow-band spectral images or the like are synthesized to produce a spectral image for diagnosis. This electronic endoscopic apparatus includes a rotation filter and performs imaging by using a plane-sequential method. The rotation filter is a filter formed by combining three kinds of narrow-band-pass filters, each transmitting light in a wavelength band different from each other. In the electronic endoscopic apparatus, the living body mucous membrane is imaged while the living body mucous membrane is sequentially illuminated with light that has been separated by being transmitted through each of the narrow-band-pass filters. Accordingly, narrow-band spectral images of the living body mucous membrane are obtained. The spectral image for diagnosis of the living body mucous membrane, which is obtained as described above, can represent a very fine structure of the living body mucous membrane, which could not be represented in a conventional apparatus.

Meanwhile, regarding an electronic endoscopic apparatus that performs imaging by using a plane-simultaneous method by placing an RGB mosaic filter, which is used in ordinary color image photography, in a solid-state imaging device, a method for obtaining an image that has a quality similar to that of the narrow-band spectral image, obtained through the narrow-band-pass filter, has been proposed. In this method, the image is obtained by performing an operation based on color image data obtained by imaging a living body mucous membrane.

The method, as described above, has been proposed by finding out a fact that spectral reflectances of the living body mucous membrane in the entire wavelength band of visible light can be substantially restored using three major components, namely the first major component through the third major component. This fact was found out by performing major component analyses for estimating the spectral reflectance of the living body mucous membrane using a multiplicity of sets of measurement data on the spectral reflectances of the living body mucous membrane in the wavelength band of visible light. In this restoration method, it is possible to obtain an image having a quality similar to that of the narrow-band spectral image in a pseudo manner by performing an operation using spectral reflection estimation matrix data and image data of each of RGB colors that has been obtained by performing imaging through an ordinary RGB mosaic filter corresponding to the three major components. The spectral reflection estimation matrix data is data obtained in advance using a multiplicity of sets of measurement data on the spectral reflectance of the living body mucous membrane (please refer to Japanese Unexamined Patent Publication No. 2003-93336 and "Analysis and Evaluation of Digital Color Image", Yoichi Miyake, University of Tokyo Press, pp. 148-153).

The spectral reflectance of a living body mucous membrane in a short wavelength band is lower than that of the living body mucous membrane in a long wavelength band, as illustrated in FIG. 4. Therefore, when reflection light reflected by the living body mucous membrane is received by an imaging device to form an image, the light receiving level of light (for example, green light and blue light) in a short wavelength band is lower than the light receiving level of light (for example, red light) in a long wavelength band. Meanwhile, an image signal obtained by receiving light of each of the colors includes a noise component, and a constant noise component is included in the noise component. The constant noise component is included at a substantially constant ratio with respect to a maximum light receiving level of light receivable at the imaging device. Specifically, when a spectral image is obtained by reading the image signal, a constant noise component is included in the spectral image at a constant ratio with respect to the maximum light receiving level regardless of the light receiving level. Therefore, the ratio of a constant noise component included in a spectral image corresponding to the short wavelength band is larger than that of a constant noise component included in a spectral image corresponding to the long wavelength band, thereby the quality of the spectral image corresponding to the short wavelength band becoming lower. Hence, there is a demand for reduction of the ratio of the constant noise component included in the spectral image corresponding to the short wavelength band.

The ratio of the constant noise component included in the spectral image corresponding to the short wavelength band might be reduced by increasing the light receiving level corresponding to the short wavelength band when an image is obtained by the imaging device. However, if the light receiving level corresponding to the short wavelength band is increased, there is a problem that the light receiving level corresponding to the long wavelength band is saturated and exceeds the maximum light receiving level.

SUMMARY OF THE INVENTION

In view of the foregoing circumstances, it is an object of the present invention to provide an electronic endoscopic apparatus that can suppress deterioration in the quality of spectral images for diagnosis.

An electronic endoscopic apparatus according to the present invention is an electronic endoscopic apparatus comprising:

a spectral image obtainment means of a plane-simultaneous method including a light receiving means for receiving reflection light in each of wavelength bands that are different from each other, and into which reflection light of illumination light, reflected by a living body mucous membrane by illumination with the illumination light, is separated, the spectral image obtainment means obtaining spectral image data representing a spectral image of the living body mucous membrane;

a spectral image data operation means for obtaining spectral operation image data representing a spectral image of the living body mucous membrane at a specific wavelength by performing a spectral image estimation operation based on the spectral image data and spectral reflection estimation matrix data that has been input and stored in advance; and a diagnostic spectral image production means for producing, based on the spectral operation image data, a spectral image of the living body mucous membrane for diagnosis, wherein the spectral image obtainment means receives the reflection light by causing ratio Hj (Hj=Js/Jp) of light receiving level Js at the light receiving means that has received reflection light in a short wavelength band on the short wavelength side of a long wavelength band, the long wavelength band being the longest wavelength band of the different wavelength bands, with respect to light receiving level Jp at the light receiving means that has received reflection light in the long wavelength band to be greater than ratio Hk (Hk=Ks/Kp) of spectral reflectance Ks in the short wavelength band in a reflection area of the reflection light on the living body mucous membrane with respect to spectral reflectance Kp in the long wavelength band in the reflection area of the reflection light on the living body mucous membrane (Hj>Hk), and wherein the spectral image data operation means performs the spectral image estimation operation by correcting the value of the spectral image data that corresponds to the short wavelength band, and that has been obtained by receiving light at the light receiving means by causing the ratio of the light receiving level in the short wavelength band with respect to the light receiving level in the long wavelength band to be greater, to the value of spectral image data that corresponds to the short wavelength, and that is obtained by receiving light at the light receiving means without causing the ratio of the light receiving level in the short wavelength band with respect to the light receiving level in the long wavelength band to increase.

The plane-simultaneous method is a method in which reflection light in wavelength bands different from each other is simultaneously received by the light receiving means. The reflection light in the wavelength bands different from each other is light into which reflection light, reflected by illuminating a living body mucous membrane with illumination light, has been separated.

The expression "by causing ratio Hj of light receiving level Js in the short wavelength band with respect to light receiving level Jp in the long wavelength band to be greater than ratio Hk of spectral reflectance Ks of the living body mucous membrane in the short wavelength band with respect to spectral reflectance Kp of the living body mucous membrane in the long wavelength band" means that the light receiving level Js in the short wavelength band is increased without reducing the light receiving level Jp in the long wavelength band, thereby causing the ratio Hj between the light receiving levels to be greater than the ratio Hk between the spectral reflectances.

The wavelength bands that are different from each other may be a red band, a green band and a blue band.

It is preferable that the spectral image obtainment means receives the reflection light in such a manner that the light receiving level in each of the different wavelength bands at the light receiving means is higher than or equal to 50% of a maximum light receiving level. It is more preferable that the spectral image obtainment means receives the reflection light in such a manner that the light receiving level in each of the different wavelength bands at the light receiving means is higher than or equal to 80% of the maximum light receiving level.

The spectral image obtainment means may receive the reflection light in such a manner that the light receiving level in the short wavelength band at the light receiving means is substantially the same as the light receiving level in the long wavelength band at the light receiving means. The expression "the light receiving level is substantially the same" means that a difference between the light receiving level in the long wavelength band and the light receiving level in the short wavelength band is within a range of ±20% of the light receiving level in the long wavelength band and preferably within a range of ±10% of the light receiving level in the long wavelength band.

The spectral image obtainment means may include an illumination means for emitting the illumination light. The illumination means may emit the illumination light in such a manner that ratio Hm of the intensity of light in the long wavelength band at the illumination means with respect to the intensity of light in the short wavelength band at the illumination means is substantially the same as the ratio Hk between the spectral reflectances. The expression "substantially the same" means that a difference between the ratio Hm and the ratio Hk is within a range of ±20% of the ratio Hk and preferably within a range of ±10% of the ratio Hk.

The illumination means may include individual light sources that emit light corresponding to the respective wavelength bands, which are different from each other.

The electronic endoscopic apparatus may include a light intensity ratio detection means for detecting a ratio of the intensity of the illumination light in the short wavelength band with respect to the intensity of the illumination light in the long wavelength band. The spectral image data operation means may perform correction in the spectral image estimation operation using the ratio detected by the light intensity ratio detection means.

The spectral image obtainment means may include a spectral mosaic filter for separating the reflection light, reflected by the living body mucous membrane, into wavelength bands different from each other. The spectral mosaic filter may be a filter in which ratio Ht of the transmittance of a spectral filter portion of the spectral mosaic filter that transmits reflection light in the long wavelength band with respect to the transmittance of a spectral filter portion of the spectral mosaic filter that transmits reflection light in the short wavelength band is substantially the same as the ratio Hk between the spectral reflectances. The expression "substantially the same" means that a difference between the ratio Ht and the ratio Hk is within a range of ±20% of the ratio Hj and preferably within a range of ±10% of the ratio Hj.

It is preferable that the illumination light is light of which the intensity is greater than or equal to 5% of the peak value in the spectral intensity distribution of the illumination light at any wavelength in a wavelength band of visible light. However, it is not necessary that the illumination light is such light.

It is preferable that the wavelength bands different from each other are wavelength bands that do not overlap with each other, and that a synthesized wavelength band, which is the sum of the different wavelength bands, covers the entire wavelength band of visible light. However, it is not necessary that the wavelength bands are such bands.

In the electronic endoscopic apparatus according to the present invention, the spectral image obtainment means obtains spectral image data by receiving reflection light by causing ratio Hj of light receiving level Js at a light receiving means which has received reflection light in a short wavelength band with respect to light receiving level Jp at the light receiving means which has received reflection light in a long wavelength band to be greater than ratio Hk of spectral reflectance Ks in the short wavelength band in a reflection area of the reflection light on the living body mucous membrane with respect to spectral reflectance Kp in the long wavelength band in the reflection area of the reflection light on the living body mucous membrane. The spectral image data operation means performs a spectral image estimation operation by correcting the value of spectral image data that corresponds to the short wavelength band, and that is obtained by receiving light at the light receiving means by causing the ratio of the light receiving level in the short wavelength band with respect to the light receiving level in the long wavelength band to be greater, to the value of spectral image data that corresponds to the short wavelength, and that is obtained by receiving light at the light receiving means without causing the ratio of the light receiving level in the short wavelength band to increase. Therefore, it is possible to reduce the ratio of the noise component included in the spectral image data corresponding to the short wavelength band. Further, it is possible to suppress deterioration in the quality of a spectral image for diagnosis that is produced based on the spectral image data.

Specifically, the spectral image data obtained by the light receiving means includes a noise component. The noise component includes two kinds of noise components, namely a noise component that increases or decreases in proportion to a fluctuation amount of the light receiving level and a constant noise component, which does not increase nor decrease in proportion to a fluctuation amount of the light receiving level. A substantially constant amount of constant noise component is included in the spectral image data regardless of the value of the light receiving level. Therefore, the ratio of a constant noise component in the value of spectral image data obtained at a high light receiving level is lower than that of a constant noise component in the value of spectral image data obtained at a low light receiving level. In other words, if spectral image data is obtained at a higher light receiving level, it is possible to reduce the ratio of a constant noise component in the value of the spectral image data than the ratio of a constant noise component in the value of spectral image data obtained at a low light receiving level.

Meanwhile, a spectral reflectance of the living body mucous membrane in a short wavelength band is lower than that of the living body mucous membrane in a long wavelength band. Further, in conventional methods, the ratio of a light receiving level in a short wavelength band with respect to a light receiving level in a long wavelength band when reflection light, reflected by the living body mucous membrane, is received by the light receiving means and the ratio of a spectral reflectance of the living body mucous membrane in the short wavelength band with respect to a spectral reflectance of the living body mucous membrane in the long wavelength band are set so that they are the same. Specifically, these ratios are set so that the color of a subject observed using the electronic endoscopic apparatus is the same as the color of the subject directly observed.

As described above, it is possible to reduce the ratio of the constant noise component included in the spectral image data corresponding to the short wavelength band by obtaining spectral image data by receiving light by causing ratio Hj of light receiving level Js corresponding to a short wavelength band with respect to light receiving level Jp corresponding to a long wavelength band to be greater than ratio Hk of spectral reflectance Ks in the short wavelength band on the living body mucous membrane with respect to spectral reflectance Kp in the long wavelength band on the living body mucous membrane. Accordingly, it is possible to perform a spectral image estimation operation using the spectral image data in the short wavelength band, of which the ratio of the constant noise component has been reduced. Therefore, it is possible to reduce the noise component included in the spectral image for diagnosis, thereby suppressing deterioration in the quality of the spectral image for diagnosis.

Further, if the wavelength bands that are different from each other are a red band, a green band and a blue band, since these wavelength bands are wavelength bands used in a conventional electronic endoscopic apparatus for observing color images, it is possible to produce the electronic endoscopic apparatus of the present invention by utilizing various elements of conventional endoscopic apparatuses. Hence, it is possible to suppress an increase in the production cost of the apparatus.

Further, if the spectral image obtainment means receives the reflection light so that the light receiving level in each of all the different wavelength bands at the light receiving means is higher than or equal to 50% of the maximum light receiving level, or preferably higher than or equal to 80% of the maximum light receiving level, it is possible to more efficiently reduce the ratio of the constant noise in the value of the spectral image data corresponding to the short wavelength band. Hence, it is possible to more efficiently suppress deterioration in the quality of the spectral image for diagnosis.

If the spectral image obtainment means receives the reflection light so that the light receiving level of the reflection light in the short wavelength band at the light receiving means is substantially the same as that of the reflection light in the long wavelength band, it is possible to further increase the light receiving level in each of the wavelength bands. Specifically, since it is necessary to receive the reflection light so that the light receiving level of the reflection light does not exceed the maximum light receiving level of the light receiving means, if a difference between the light receiving levels in different wavelength bands is reduced, the light receiving means can receive the reflection light at a higher light receiving level. For example, if the light receiving levels in different wavelength bands are the same, it is possible to receive light at the maximum light receiving level of the light receiving means. Accordingly, it is possible to further reduce the ratio of the constant noise in the value of the spectral image data, thereby further suppressing deterioration in the quality of the spectral image for diagnosis.

Here, if the spectral image data obtainment means includes an illumination means for emitting illumination light, and the illumination means emits the illumination light so that ratio Hm of the intensity of light in the long wavelength band at the illumination means with respect to the intensity of light in the short wavelength band at the illumination means is substantially the same as the ratio Hk between the spectral reflectances, it is possible to more efficiently reduce the ratio of the constant noise in the value of the spectral image data corresponding to the short wavelength band. Accordingly, it is possible to more efficiently suppress deterioration in the quality of the spectral image for diagnosis. Further, if the illumination means includes individual light sources that emit light corresponding to respective wavelength bands, it is possible to more easily obtain illumination light that has the spectral intensity distribution, as described above.

Further, if a light intensity ratio detection means for detecting a ratio of the intensity of illumination light in the short wavelength band with respect to the intensity of the illumination light in the long wavelength band is further provided, and if the spectral image data operation means performs correction in the spectral image estimation operation using the ratio detected by the light intensity ratio detection means, it is possible to more efficiently perform the spectral image estimation operation. Hence, it is possible to more efficiently suppress deterioration in the quality of the spectral image for diagnosis.

Further, if the spectral image obtainment means includes a spectral mosaic filter for separating the reflection light, reflected by the living body mucous membrane, into wavelength bands that are different from each other, and if the spectral mosaic filter is formed so that ratio Ht of the transmittance of a spectral filter portion that transmits reflection light in the long wavelength band with respect to the transmittance of a spectral filter portion that transmits reflection light in the short wavelength band is substantially the same as the ratio Hk between the spectral reflectances, it is possible to more efficiently increase the ratio of the light receiving level in the short wavelength band at the light receiving means with respect to the light receiving level in the long wavelength band at the light receiving means. Hence, it is possible to more efficiently suppress deterioration in the quality of the spectral image for diagnosis.

BRIEF DESCRIPTION OF THE DRAWINGS

FIG. 10 is a diagram illustrating a ratio of constant noise in a corrected light receiving level.

DESCRIPTION OF THE PREFERRED EMBODIMENTS

Figure 1:
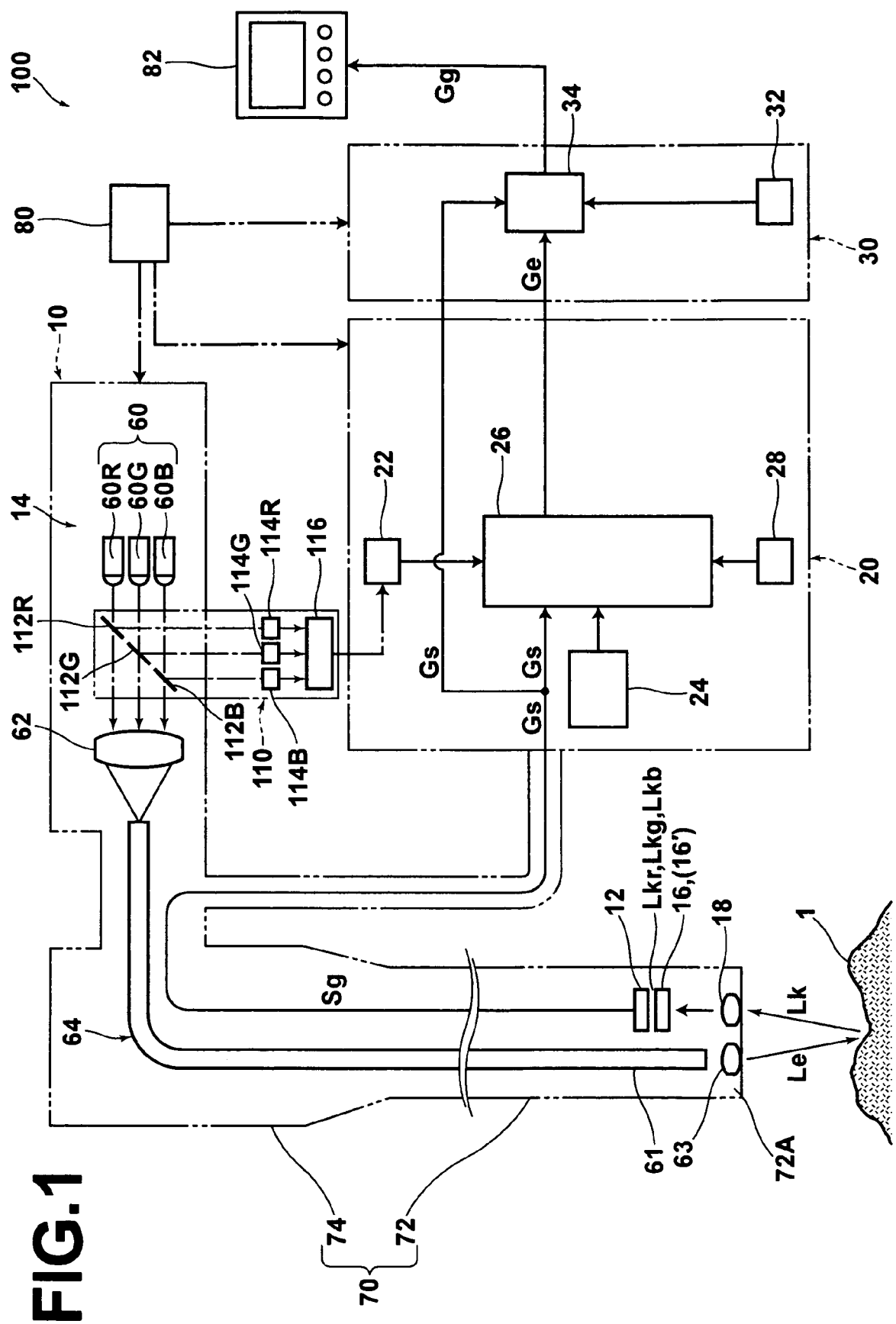
FIG. 1 is a schematic block diagram illustrating the configuration of an electronic endoscopic apparatus in an embodiment of the present invention.
Figure 2:
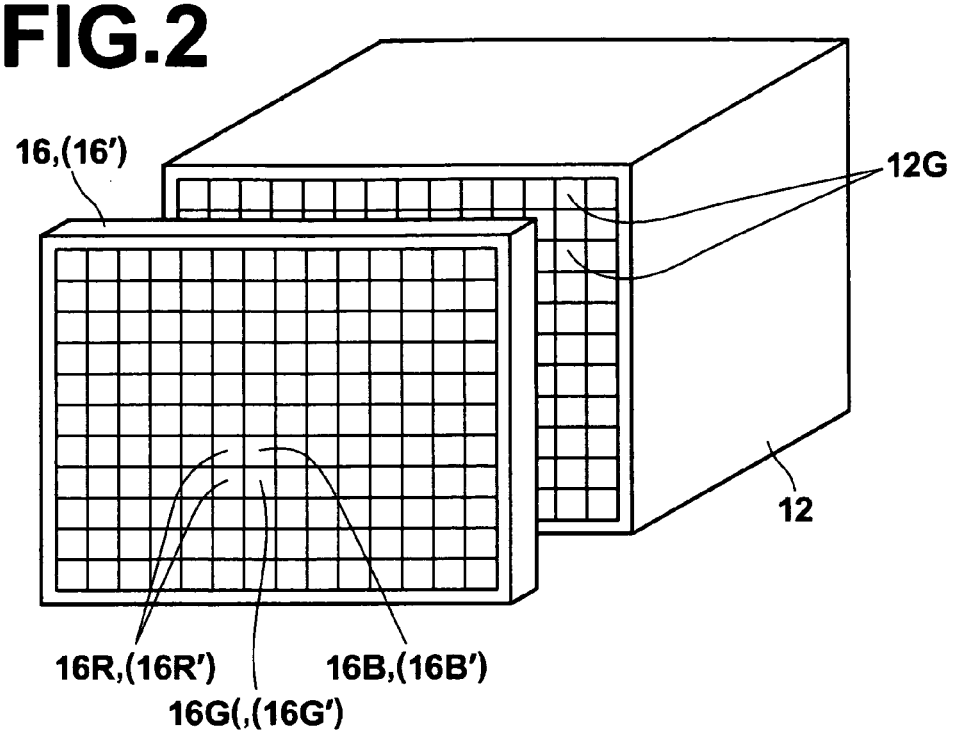
FIG. 2 is an enlarged perspective view of an imaging unit and a spectral mosaic filter.

Hereinafter, embodiments of the present invention will be described with reference to the attached drawings. FIG. 1 is a schematic block diagram illustrating the configuration of an electronic endoscopic apparatus in an embodiment of the present invention. FIG. 2 is an enlarged perspective view of an imaging unit and a spectral mosaic filter.

In the electronic endoscopic apparatus of the present invention, when a spectral image of a living body mucous membrane is obtained, spectral image data representing the spectral image is obtained by performing imaging with an emphasis on a short wavelength band relative to a long wavelength. Then, spectral operation image data representing a spectral image at a specific wavelength is obtained by performing a spectral image estimation operation. The spectral image estimation operation is performed by correcting the emphasized amount in the short wavelength band using the spectral image data. Then, a spectral image for diagnosis is produced based on the spectral operation image data.

As illustrated in FIG. 1, an electronic endoscopic apparatus 100, which is an embodiment of the present invention, includes a spectral image obtainment means 10 that has an imaging unit 12. The imaging unit 12 includes a CCD (charge coupled device), which is a light receiving means, or the like. The light receiving means receives reflection light Lkr, Lkg and Lkb in respective wavelength bands, which are different from each other, namely a red band, a green band and a blue band, into which reflection light Lk of illumination light Le has been separated. The illumination light Le is light with which a living body mucous membrane 1 has been illuminated, and the reflection light Lk is light reflected by the living body mucous membrane 1. The spectral image obtainment means 10 is a spectral image obtainment means of a plane-simultaneous method, and obtains spectral image data Gs, which represents a spectral image of the living body mucous membrane 1. The electronic endoscopic apparatus 100 also includes a spectral image data operation means 20 and a diagnostic spectral image production means 30. The spectral image data operation means 20 obtains spectral operation image data Ge representing a spectral image of the living body mucous membrane at a specific wavelength by performing a spectral image estimation operation based on the spectral image data Gs and spectral reflection estimation matrix data that has been input and stored in advance. The diagnostic spectral image production means 30 produces a spectral image of the living body mucous membrane 1 for diagnosis based on the spectral operation image data Ge.

The spectral image obtainment means 10 receives the reflection light by causing ratio Hj (Hj=Js/Jp) of light receiving level Js at the imaging unit 12 that has received reflection light in a short wavelength band on the short wavelength side of a long wavelength band of different wavelength bands with respect to light receiving level Jp at the imaging unit 12 that has received reflection light in the long wavelength band to be greater than ratio Hk (Hk=Ks/Kp) of spectral reflectance Ks in the short wavelength band in a reflection area of the reflection light on the living body mucous membrane 1 with respect to spectral reflectance Kp in the long wavelength band in the reflection area of the reflection light on the living body mucous membrane 1 (Hj>Hk). Here, the long wavelength band is the longest wavelength band. The spectral image obtainment means 10 receives the reflection light at the imaging unit 12 by causing the ratio Hj between the light receiving levels to be greater than the ratio Hk between the spectral reflectances without lowering the light receiving level Jp at the imaging unit 12 that has received reflection light in the long wavelength band.

The spectral image data operation means 20 performs a spectral image estimation operation by correcting the value of spectral image data that corresponds to the short wavelength band, and that is obtained by receiving light in such a manner that the ratio Hj between the light receiving levels is greater than the ratio Hk between the spectral reflectances, to the value of spectral image data that corresponds to the short wavelength, and that is obtained by receiving light at the light receiving means without causing the ratio of the light receiving level in the short wavelength band with respect to the light receiving level in the long wavelength band to increase.

The spectral image obtainment means 10 will be described. The spectral image obtainment means 10 includes the imaging unit 12, which is the light receiving means, an illumination means 14 and a spectral mosaic filter 16. The illumination means 14 emits the illumination light, and the spectral mosaic filter 16 separates reflection light Lk reflected by the living body mucous membrane 1 into light in wavelength bands that are different from each other, namely a red band, a green band and a blue band. The spectral mosaic filter 16 is placed in front of a light receiving surface of the imaging unit 12.

The illumination means 14 emits illumination light Le that has spectral intensity distribution in which ratio Hm of the intensity of illumination light in the long wavelength band with respect to the intensity of illumination light in the short wavelength band is substantially the same as the ratio Hk between the spectral reflectances. The illumination means 14 is formed by individual light sources that emit light in wavelength bands that are different from each other. The illumination means 14 includes a light source unit 60 and an illumination light propagation optical system 64. The light source unit 60 includes a red light source 60R, a green light source 60G and a blue light source 60B. The red light source 60R emits red light, which is light in a red band. The green light source 60G emits green light, which is light in a green band. The blue light source 60B emits blue light, which is light in a blue band. The illumination light propagation optical system 64 propagates the red light, the green light and the blue light emitted from the light source unit 60. The illumination light propagation optical system 64 will be described later.

The spectral image obtainment means 10 includes an endoscope unit 70. The endoscope unit 70 includes an insertion portion 72 and an angle operation portion 74. The imaging unit 12, the spectral mosaic filter 16 and the like are housed in the insertion portion 72. The insertion portion 72 is bendable, and it has a long thin shape. The angle operation portion 74 is connected to and integrated with the insertion portion 72. The angle operation portion 74 operates the bending motion or the like of the insertion portion 72. The angel operation portion 74 is positioned on the light source 60 side of the endoscope unit 70, and the insertion portion 72 is inserted into the body cavity of a patient (test body).

A leading edge portion 72A forms the leading edge of the insertion portion 72, which is inserted into the body cavity of the patient, and an object lens 18 is placed at the leading edge portion 72A. The object lens 18 forms an image of the living body mucous membrane 1, which is an observation object, and which has been illuminated with the illumination light Le, on the imaging unit 12 through the spectral mosaic filter 16.

Further, a signal line Sg and the illumination light propagation optical system 64 are provided in the endoscope unit 70. The signal line Sg is a signal line for transmitting the spectral image data obtained at the imaging unit 12 to the spectral image data operation means 20. The illumination light propagation optical system 64 propagates light emitted from the light source 60. The signal line Sg and the illumination light propagation optical system 64 are provided in an area from the angle operation portion 74 to the leading edge portion 72A of the insertion portion 72.

The illumination light propagation optical system 64 includes a condensing lens 62, a light guide 61 and an illumination lens 63. The condensing lens 62 causes red light, green light and blue light emitted from the light source unit 60 to enter an end of the light guide 61, which will be described later. The light guide 61 forms the illumination light propagation optical system 64. The light guide 61 guides the light of each color that has been condensed by the condensing lens 62, and that has entered the end of the light guide 61, to the leading edge portion 72A. The illumination lens 63 is placed at the leading edge portion 72A. The illumination lens 63 transmits light flux emitted from the light guide 61 and increases the diameter of the light flux. Then, the living body mucous membrane 1 is illuminated with the light flux.

The spectral transmittance of the illumination light propagation optical system 64 and that of the object lens 18 are constant in the wavelength band of visible light. Specifically, the transmittance of the illumination light propagation optical system 64 and that of the object lens 18 are constant in the wavelength band of visible light regardless of the wavelengths.

The intensity of green light emitted from the green light source 60G is greater than that of red light emitted from the red light source 60R, and the intensity of blue light emitted from the blue light source 60B is greater than that of red light emitted from the red light source 60R. The intensity of the light of each of the colors is set in such a manner so as to illuminate the living body mucous membrane 1 with illumination light Le that has spectral intensity distribution, in which the intensities of light in the green band and the blue band, which are short wavelength band, are greater than the intensity of light in the red band, which is a long wavelength band.

In the imaging unit 12, a multiplicity of light receiving pixels 12G are two-dimensionally arranged, as illustrated in FIG. 2. Further, in the spectral mosaic filter 16, a multiplicity of red-band-pass filter portions 16R, a multiplicity of green-band-pass filter portions 16G and a multiplicity of blue-band-pass filter portions 16B are placed in such a manner that they correspond to the two-dimensionally-arranged light receiving pixels 12G.

The transmittance of the red-band-pass filter portion 16R with respect to light in a red band, that of the green-band-pass filter portion 16G with respect to light in a green band and that of the blue-band-pass filter portion 16B with respect to light in a blue band are the same.

Next, the spectral image data operation means 20 will be described. For example, the spectral image data operation means 20 corrects the value of spectral image data that corresponds to a green band, and that has been obtained by causing a ratio of a light receiving level of light in the green band with respect to a light receiving level of light in a red band at the time of receiving the reflection light Lk at the imaging unit 12 to be greater, to the value of spectral image data that corresponds to the green band, and that is obtained by receiving light at the imaging unit 12 without causing the ratio to increase. Further, the spectral image data operation means 20 corrects the value of spectral image data that corresponds to a blue band, and that has been obtained by causing a ratio of a light receiving level of light in the blue band with respect to a light receiving level of light in a red band to be greater, to the value of spectral image data corresponding to the blue band obtained by receiving light at the imaging unit 12 without causing the ratio to increase. Accordingly, the spectral image data operation means 20 performs the spectral image estimation operation.

The spectral image data operation means 20 includes a ratio comparison information storage unit 22, a matrix data storage unit 24, a specific wavelength specification switch 28 and an operation execution unit 26. The ratio comparison information storage unit 22 stores ratio comparison information representing a ratio between light receiving levels with respect to the ratio between the spectral reflectances. The matrix data storage unit 24 stores spectral reflection estimation matrix data that has been prepared in advance. The specific wavelength specification switch 28 specifies a specific wavelength when spectral operation image data Ge is obtained by performing a spectral image estimation operation. The operation execution unit 26 executes a spectral image estimation operation for the specific wavelength specified by the specific wavelength specification switch 28 using the ratio comparison information, stored in the ratio comparison information storage unit 22, the spectral reflection estimation matrix data, stored in the matrix data storage unit 24, and the spectral image data Gs, obtained by the spectral image obtainment means 10.

It is preferable that the spectral reflection estimation matrix data is prepared in advance for each organ. For example, it is preferable that one kind of spectral reflection estimation matrix data is prepared to produce a diagnostic spectral image of the mucous membrane of the stomach and that one kind of spectral reflection estimation matrix data is prepared to produce a diagnostic spectral image of the mucous membrane of the intestines or the like.

The operation execution unit 26 may perform an actual operation in any manner as long as the spectral image estimation operation is substantially performed. The spectral image estimation operation is performed by correcting the value of the spectral image data Gs. For example, a coefficient of the spectral reflection estimation matrix data may be changed by a correction amount without directly correcting the value of the spectral image data Gs, obtained by the spectral image obtainment means 10. Specifically, the correction amount for the spectral image data Gs may be allocated to appropriate points in the spectral image estimation operation for the convenience of the operation.

The diagnostic spectral image production means 30 includes an image synthesis unit 34 and an image synthesis selection switch 32. The kind of a spectral image for diagnosis that will be produced by the image synthesis unit 34 and displayed on a display monitor 82 is determined by switching the image synthesis selection switch 32.

The spectral operation image data Ge and the spectral image data Gs are input to the diagnostic spectral image production means 30. The spectral operation image data Ge is data obtained by the spectral image data operation means 20, and the spectral image data Gs is data obtained by the spectral image obtainment means 10. Then, the image synthesis unit 34 produces, based on the input spectral operation image data Ge and the input spectral image data Gs, spectral image data Gg for diagnosis corresponding to the setting by the image synthesis selection switch 32 and outputs the produced data to the display monitor 82. When the diagnostic spectral image data Gg is input to the display monitor 82, a spectral image for diagnosis representing the living body mucous membrane 1 is displayed on the display monitor 82.

The operation of each of the units and the timing of each operation are controlled by a controller 80.

Next, the action of the electronic endoscopic apparatus 100 in the present embodiment will be described.

First, a major component analysis for obtaining spectral reflection estimation matrix data that is used in the spectral image estimation operation will be described.

The spectral reflectance of a measurement object, such as a living body mucous membrane, in a wavelength band of visible light, can be indicated by reflectance that is measured in a wavelength band from approximately 400 nm to approximately 700 nm at wavelength intervals of 5 nm or 10 nm. Specifically, the spectral reflectance can be represented by a 61-dimensional or 31-dimensional discrete value of reflectance at each of the wavelengths. The spectral reflectance is obtained by measuring a ratio of the intensity of reflection light reflected by the living body mucous membrane 1 with respect to the intensity of white light at each of the wavelengths.

Meanwhile, it is possible to restore spectral reflectance in the entire wavelength band of visible light, based on spectral reflectance data that is less than the 61-dimensional or 31-dimensional discrete value of reflectance, by performing a major component analysis on a multiplicity of sets of spectral reflectance data regarding the living body mucous membrane, which is the measurement object.

For example, when the measurement object is a Munsell color chart, a result that spectral reflectance of the Munsell color chart in the entire wavelength band of visible light can be substantially restored by utilizing eight kinds of major components, namely the first major component through the eighth major component, has been obtained. The spectral reflectance is restored by performing a major component analysis in which a multiplicity of spectral reflectances of the Munsell color chart is measured.

Further, when the measurement object is a living body mucous membrane, such as the stomach wall, a result that 99% of the spectral reflectance of the living body mucous membrane in the entire wavelength band of visible light can be restored by utilizing three kinds of major components, namely the first major component through the third major component, has been obtained. The spectral reflectance is restored by performing a major component analysis in which a multiplicity of spectral reflectances of the living body mucous membrane is measured.

The expression that the spectral reflectance of the measurement object can be estimated based on the three kinds of major components refers to that spectral reflectance in the entire wavelength band of visible light can be estimated based on information about the intensity of reflection light, reflected by the living body mucous membrane 1, in each of three kinds of wavelength bands, namely a red band, a green band and a blue band, for example. Specifically, it is possible to estimate spectral reflectance in the entire wavelength band of visible light at wavelength intervals of 5 nm or 10 nm.

When a spectral reflection light intensity ratio matrix, which represents the ratio of spectral reflectances of a living body mucous membrane in three kinds of wavelength bands, namely a red band, a green band and a blue band, is C, a specific wavelength matrix, which represents the ratio of spectral reflectances to be obtained at specific wavelengths is F, and spectral reflection estimation matrix data is A, the following equations are satisfied:

$$CA = F,$$

$$C = (\vec{RGB}),$$

$$A = \begin{pmatrix} a_1 & a_2 & a_3 \\ b_1 & b_2 & b_3 \\ c_1 & c_2 & c_3 \end{pmatrix}, \text{ and}$$

$$F = (\vec{F_1}\vec{F_2}\vec{F_3}).$$

Specifically, the spectral reflection light intensity ratio matrix C is a matrix representing the ratio of the intensities of reflection light, reflected by the living body mucous membrane, in three kinds of wavelength bands when the living body mucous membrane is illuminated with white light. Further, the specific wavelength matrix F is a matrix representing the ratio of the intensities of reflection light, reflected by the living body mucous membrane, at specific wavelengths when the living body mucous membrane is illuminated with white light. Here, the spectral reflection estimation matrix data A can be obtained in advance by performing measurement on a multiplicity of living body mucous membranes. Further, the spectral reflection light intensity ratio matrix C can be obtained by measurement. Therefore, it is possible to obtain the specific wavelength matrix F. Specifically, it is possible to obtain the ratio of spectral reflectances of a living body mucous membrane at three kinds of specific wavelengths, namely 600 nm, 540 nm and 420 nm. More specifically, it is possible to obtain the ratio of spectral reflectances of the living body mucous membrane at three kinds of specific narrow wavelength bands, namely 600 nm±5 nm, 540 nm±5 nm and 420 nm±5 nm.

Therefore, it is possible to estimate the ratio of the intensities of reflection light, which is reflected by the living body mucous membrane 1 by illumination of the living body mucous membrane 1 with white light, at specific wavelengths. The ratio can be estimated using the intensity of reflection light in each of wavelength bands, namely a red band, a green band and a blue band, reflected by the living body mucous membrane 1 when the living body mucous membrane 1 is illuminated with white light, and spectral reflection estimation matrix data that has been prepared in advance.

The spectral image estimation operation, as described above, corresponds to the spectral image estimation operation performed by the spectral image data operation means 20. Here, a well-known method may be adopted to obtain a spectral image in a specific wavelength band by performing the spectral image estimation operation.

Figure 3:
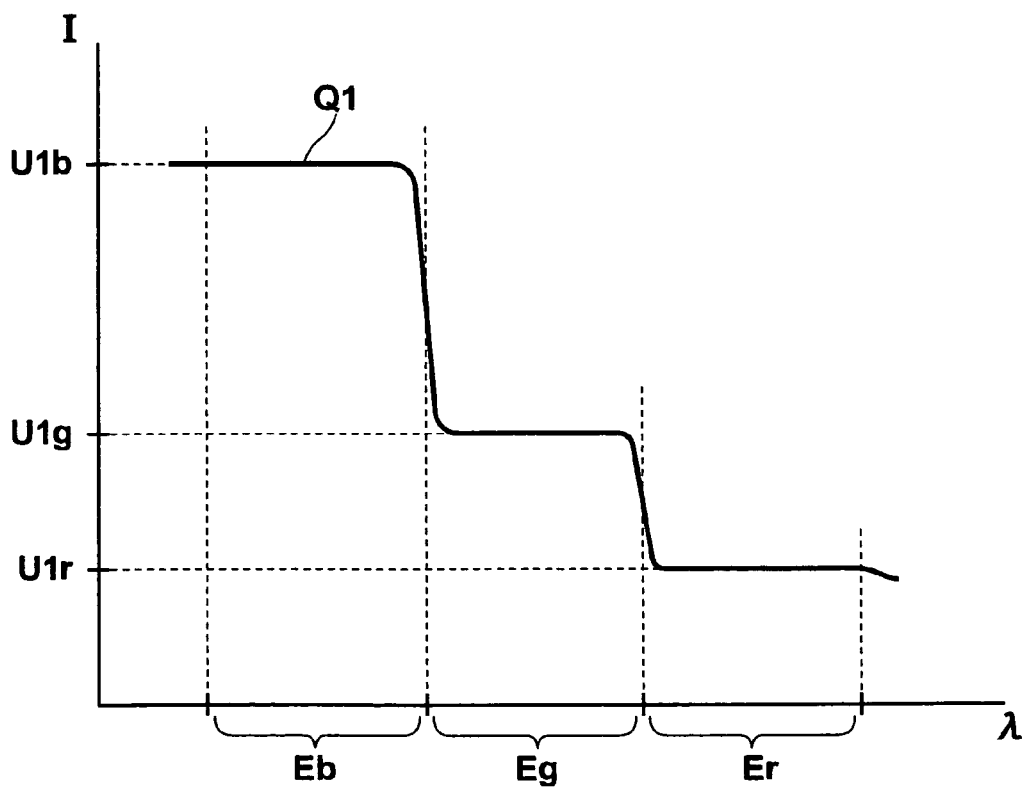
FIG. 3 is a diagram illustrating the spectral intensity distribution of illumination light.
Figure 4:
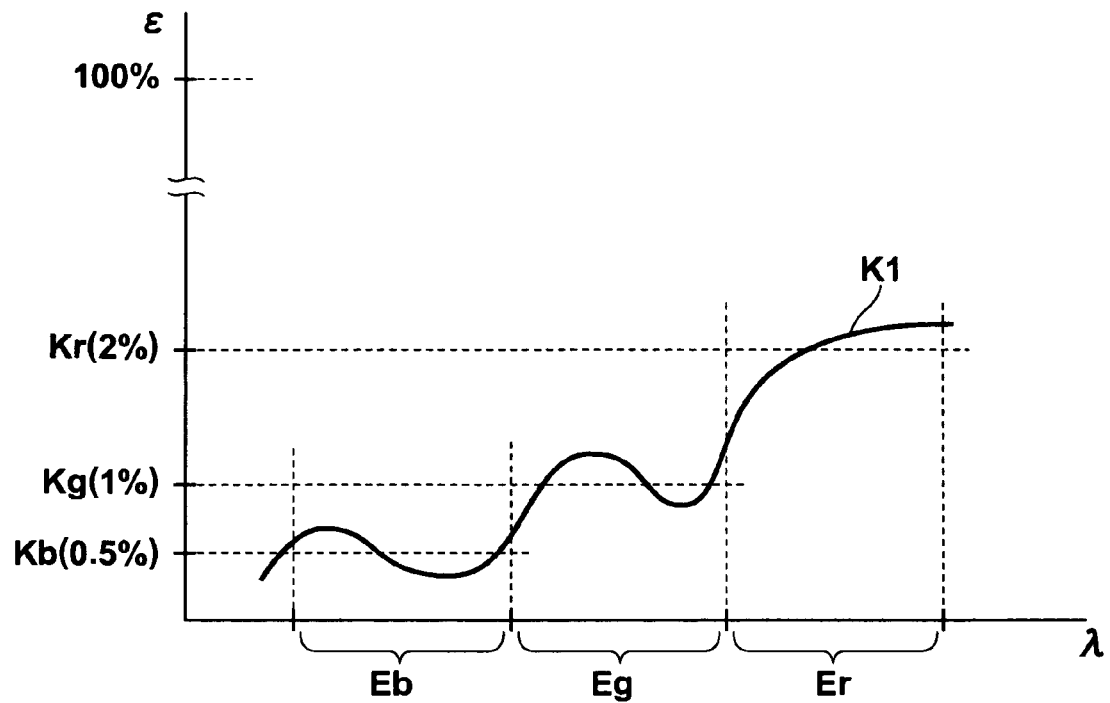
FIG. 4 is a diagram illustrating spectral reflectances of a living body mucous membrane.
Figure 5:
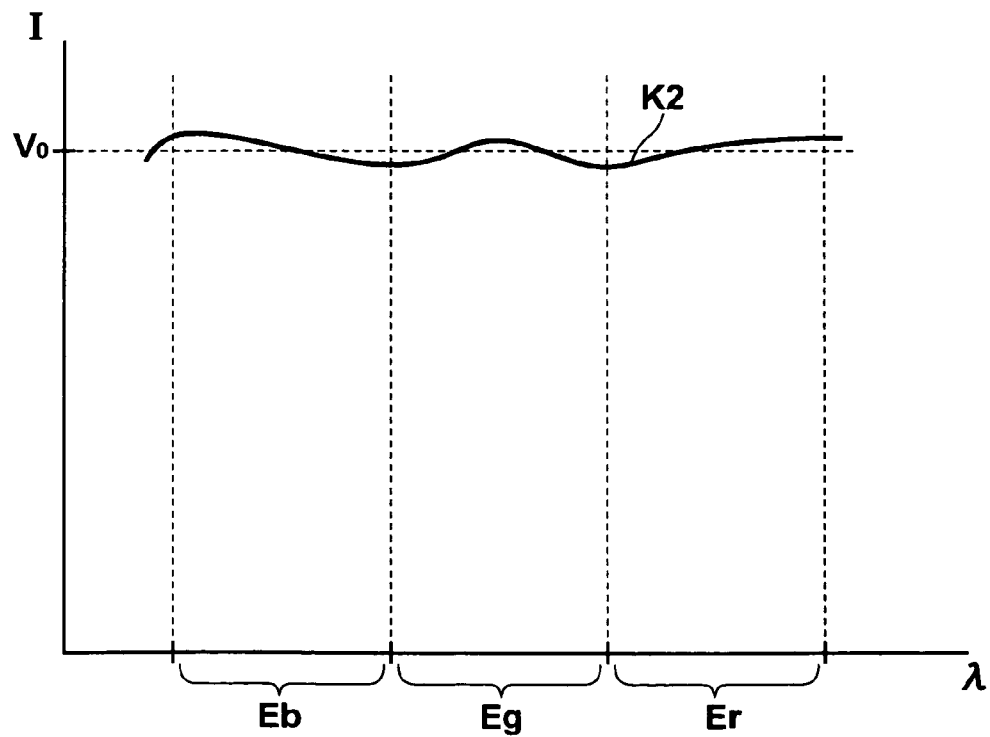
FIG. 5 is a diagram illustrating the intensity of light when reflection light reflected by a living body mucous membrane is received at an imaging unit.
Figure 6:
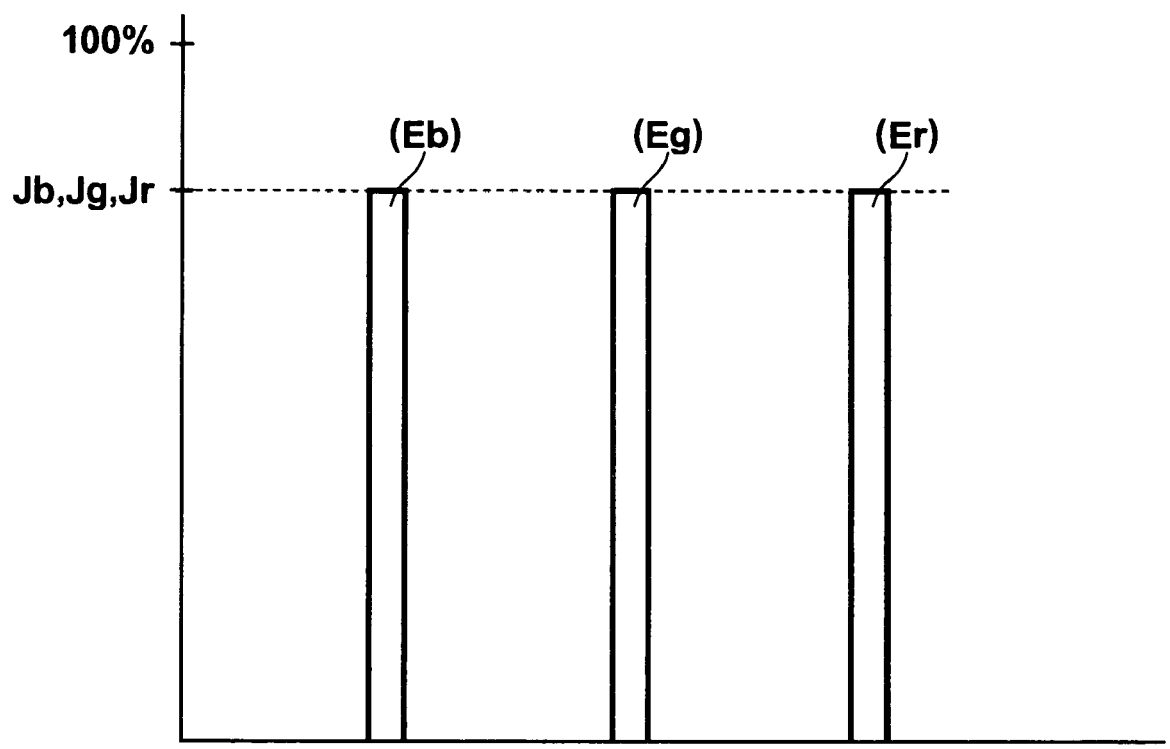
FIG. 6 is a diagram illustrating a light receiving level at the imaging unit, which has received reflection light reflected by the living body mucous membrane.
Figure 7A:
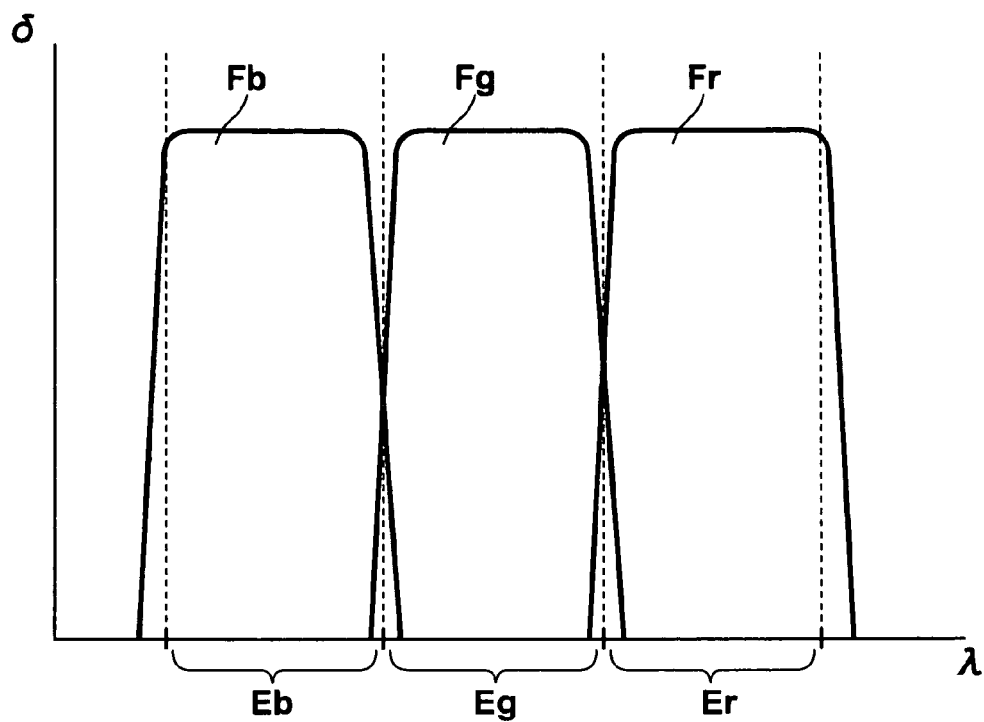
FIG. 7A is a diagram illustrating a spectral transmittance characteristic at each filter portion.
Figure 7B:
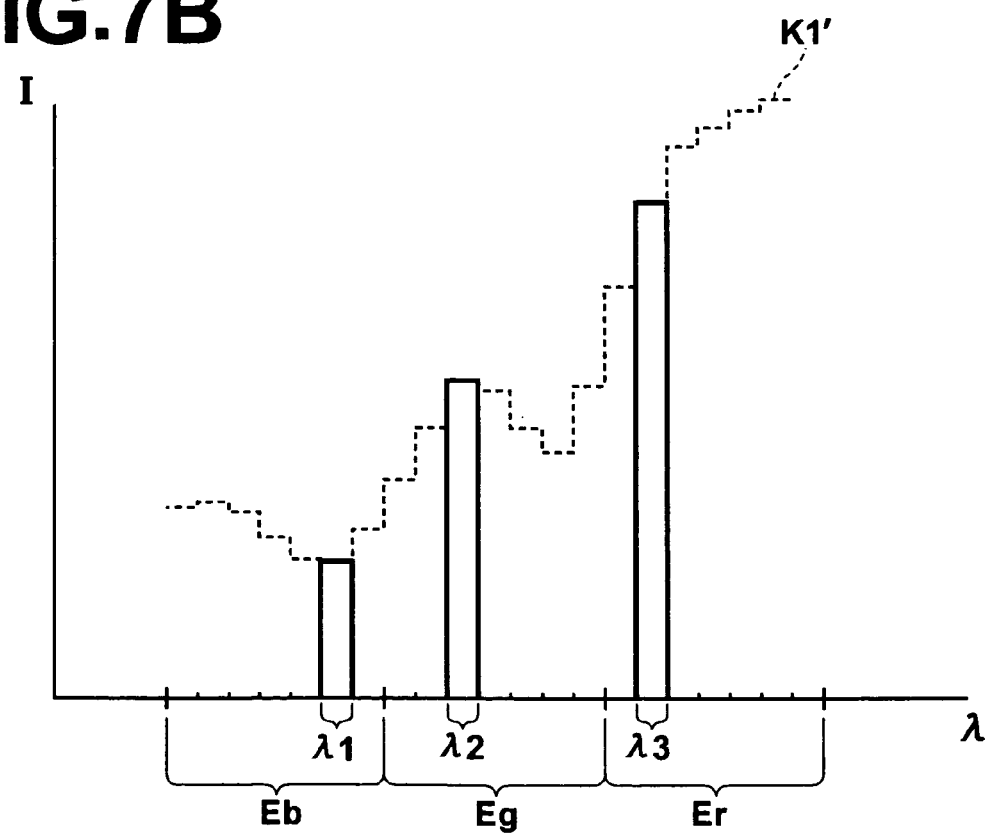
FIG. 7B is a diagram illustrating the intensities of reflection light, reflected by the living body mucous membrane, at specific wavelengths, the intensities being obtained by performing a spectral image estimation operation.

Next, a case in which a spectral image for diagnosis is obtained by the electronic endoscopic apparatus 100 by applying the spectral image estimation operation technique will be described. FIG. 3 is a diagram illustrating the spectral intensity distribution of illumination light. FIG. 4 is a diagram illustrating spectral reflectance of a living body mucous membrane. FIG. 5 is a diagram illustrating the intensity of light when reflection light reflected by a living body mucous membrane is received at an imaging unit. FIG. 6 is a diagram illustrating a light receiving level at the imaging unit, which has received reflection light reflected by the living body mucous membrane. FIG. 7A is a diagram illustrating a spectral transmittance characteristic at each filter portion. FIG. 7B is a diagram illustrating the intensities of reflection light, reflected by the living body mucous membrane, at specific wavelengths. The intensities are obtained by performing a spectral image estimation operation.

In FIG. 3, the vertical axis I represents the intensity of light and the horizontal axis λ represents wavelength. In FIG. 4, the vertical axis γ represents reflectance and the horizontal axis λ represents wavelength. In FIG. 5, the vertical axis I represents the intensity of light and the horizontal axis λ represents wavelength. In FIG. 6, the vertical axis represents light receiving levels, and a light receiving level in a blue band, a light receiving level in a green band and a light receiving level in a red band are shown side by side in the direction of the horizontal axis. In FIG. 7A, the vertical axis δ represents transmittance and the horizontal axis λ represents wavelength. In FIG. 7B, the vertical axis I represents the intensity of light and the horizontal axis λ represents wavelength.

The red light source 60R, the green light source 60G and the blue light source 60B form the light source unit 60 of the illumination means 14. Red light is emitted from the red light source 60R, green light is emitted from the green light source 60G and blue light is emitted from the blue light source 60B. The red light, the green light and the blue light are emitted simultaneously. Each of the red light, the green light and the blue light are transmitted through the illumination light propagation optical system 64 and synthesized. Illumination light Le is synthesized by combining the red light, the green light and the blue light, and emitted from the leading edge portion 72A to illuminate the living body mucous membrane 1.

As indicated by line Q1 in FIG. 3, in the spectral intensity distribution of the illumination light Le, the intensity of light in the green band Eg and the intensity of light in the blue band Eb are greater than the intensity of light in the red band Er. Further, the intensity of light in the blue band Eb is greater than the intensity of light in the green band Eg. The ratio between the intensity U1r of light in the red band Er and the intensity U1g of light in the green band Eg, U1r:U1g is 1:2. Further, the ratio between the intensity U1r of light in the red band Er and the intensity U1b of light in the blue band Eb, U1r:U1b is 1:4. Therefore, the color of the illumination light Le is not white but a color close to blue green.

As the intensity of the illumination light in each wavelength band, an average value or the like in each of the wavelength bands, namely the red band Er, the green band Eg and the blue band Eb, may be adopted, for example.

Meanwhile, the spectral reflectance of the living body mucous membrane 1 corresponding to the spectral intensity distribution of the reflection light of the white light, namely the light reflected by the living body mucous membrane 1 by illumination of the living body mucous membrane 1 with the white light, is greater in a long wavelength band than in a short wavelength band, as indicated by line K1 in FIG. 4. The spectral reflectance of the living body mucous membrane 1 has been measured in advance. The spectral reflectance Kr of light in the red band Er is approximately 2%. The spectral reflectance Kg of light in the green band Eg is approximately 1%, and the spectral reflectance Kb of light in the blue band Eb is approximately 0.5%. Therefore, the ratio between the spectral reflectance Kr of light in the red band Er and the spectral reflectance Kg of light in the green band Eg, Kr:Kg is 1:0.5. Further, the ratio between the spectral reflectance Kr in the red band Er and the spectral reflectance Kb in the blue band Eb, Kr:Kb is 1:0.25.

As the reflectance of the living body mucous membrane 1 in each of the wavelength bands, an average value or the like of spectral reflectance in each of the wavelength bands, namely the red band Er, the green band Eg and the blue band Eb, may be adopted.

When the living body mucous membrane 1 is illuminated with the illumination light Le, reflection light Lk is reflected from the living body mucous membrane 1. The reflection light Lk is transmitted through the object lens 18. Further, the reflection light Lk is transmitted through the spectral mosaic filter 16, and separated into light in the red band Er, light in the green band Eg and light in the blue band Eb. Then, an image is formed on the imaging unit 12.

Here, the living body mucous membrane 1, which has a spectral reflectance characteristic indicated by line K1 in FIG. 4, is illuminated with the illumination light Le that has the spectral intensity distribution indicated by line Q1 in FIG. 3. The spectral reflection light intensity distribution of the reflection light Lk, reflected by the living body mucous membrane 1, shows an approximately constant light intensity value $V_o$, as indicated by line K2 in FIG. 5.

Therefore, as illustrated in FIG. 6, the light receiving level Jr at the imaging unit 12 that has received the reflection light Lkr in the red band Er, the light receiving level Jg at the imaging unit 12 that has received the reflection light Lkg in the green band Eg, and the light receiving level Jb at the imaging unit 12 that has received the reflection light Lkb in the blue band Eb are at a substantially constant value.

Each of the light receiving levels Jr, Jg and Jb represents a light receiving level in respective wavelength bands when the maximum light receiving level, at which light can be received by the imaging unit 12 without saturation, is 100%. The substantially constant light receiving level at the imaging unit 12 is approximately 80%, for example.

Specifically, regarding the red band, which is a long wavelength band, and the green band, which is a short wavelength band, the spectral image obtainment means 10 receives the reflection light Lk by causing ratio Hjg (Hjg=Jg/Jr=1, please refer to FIG. 6) of light receiving level Jg (Jg=80%) at the imaging unit 12 that has received reflection light Lkg in a green band Eg with respect to light receiving level Jr (Jr=80%) at the imaging unit 12 that has received reflection light Lkr in a red band Er to be greater than ratio Hkg (Hkg=Kg/Kr=0.5, please refer to FIG. 4) of spectral reflectance Kg (1%) in the green band Eg in the reflection area of the reflection light Lk on the living body mucous membrane 1 with respect to spectral reflectance Kr (2%) in the red band Er in the reflection area of the reflection light Lk on the living body mucous membrane 1 (Hjg=1>Hkg=0.5). The spectral image obtainment means 10 causes the light receiving level of light in the green band, which is a short wavelength band, at the imaging unit 12 to be substantially the same as the light receiving level of light in the red band, which is a long wavelength band, at the imaging unit 12.

Further, regarding the red band, which is a long wavelength band, and the blue band, which is a short wavelength band, the spectral image obtainment means 10 receives the reflection light Lk by causing ratio Hjb (Hjb=Jb/Jr=1, please refer to FIG. 6) of light receiving level Jb (Jb=80%) at the imaging unit 12 that has received reflection light Lkb in a blue band Eb with respect to light receiving level Jr (Jr=80%) at the imaging unit 12 that has received reflection light Lkr in the red band Er to be greater than ratio Hkb (Hkb=Kb/Kr=0.25, please refer to FIG. 4) of spectral reflectance Kb (0.5%) in the blue band Eb in the reflection area of the reflection light Lk on the living body mucous membrane 1 with respect to spectral reflectance Kr (2%) in the red band Er in the reflection area of the reflection light Lk on the living body mucous membrane 1 (Hjb=1>Hkb=0.25). The spectral image obtainment means 10 causes the light receiving level of light in the blue band, which is a short wavelength band, at the imaging unit 12 to be substantially the same as the light receiving level in the red band, which is a long wavelength band, at the imaging unit 12.

Regarding the red band and the green band, the ratio Hjg=1 between the light receiving levels is twice the ratio Hkg=0.5 between the spectral reflectances. Further, regarding the red band and the blue band, the ratio Hjb=1 between the light receiving levels is four times greater than the ratio Hkb=0.25 between the spectral reflectances. When the intensity of the illumination light in the red band and the light receiving level in the red band are used as standards, as described above, the intensity of the illumination light in the green band is twice that of the illumination light in the red band. Therefore, the light receiving level in the green band is also twice the light receiving level in the red band. Further, the intensity of the illumination light in the blue band is four times greater than that of the illumination light in the red band. Therefore, the light receiving level in the blue band is also four times higher than the light receiving level in the red band.

Information about the value of the ratio Hkg between the spectral reflectances with respect to the ratio Hjg between the light receiving levels regarding the red band and the green band and information about the value of the ratio Hkb between the spectral reflectances with respect to the ratio Hjb between the light receiving levels regarding the red band and the blue band are stored in the ratio comparison information storage unit 22 in advance.

The illumination means 14 of the spectral image obtainment means 10 emits illumination light. The illumination light is light in which the ratio Hm (Hm=1/2) is substantially the same as the ratio Hk (Hk=1%/2%=1/2). The ratio Hm is a ratio of the intensity of light in a red band, which is a long wavelength band, at the illumination means 14 with respect to the intensity of light in a green band, which is a short wavelength band, at the illumination means 14. The ratio Hk is a ratio of the spectral reflectance in a green band, which is a short wavelength band, in a reflection area of the reflection light on the living body mucous membrane 1 with respect to the spectral reflectance in the red band, which is a long wavelength band, in the reflection area of the reflection light on the living body mucous membrane 1.

Further, the illumination means 14 of the spectral image obtainment means 10 emits illumination light. The illumination light is light in which the ratio Hm (Hm=1/4) is substantially the same as the ratio Hk (Hk=0.5%/2%=1/4). The ratio Hm is a ratio of the intensity of light in a red band, which is a long wavelength band, at the illumination means 14 with respect to the intensity of light in a blue band, which is a short wavelength band, at the illumination means 14. The ratio Hk is a ratio of the spectral reflectance in the blue band, which is a short wavelength band, in a reflection area of the reflection light on the living body mucous membrane 1 with respect to the spectral reflectance in the red band, which is a long wavelength band, in a reflection area of the reflection light on the living body mucous membrane 1.

Spectral image data Gs, which is obtained by the imaging means 12, and which represents the living body mucous membrane 1, is sent to the spectral image data operation means 20 through the signal line Sg. The spectral image data Gs is also sent to the diagnostic spectral image production means 30.

When the spectral image data Gs is input to the spectral image data operation means 20, the spectral image data operation means 20 performs a spectral image estimation operation to obtain spectral operation image data Ge, which represents spectral image at a specific wavelength specified by the specific wavelength specification switch 28.

The spectral image data Gs of the living body mucous membrane 2, obtained by imaging the living body mucous membrane 1, is not obtained by illuminating the living body mucous membrane 1 with white light. In other words, the spectral image data Gs does not correspond to the spectral reflectance of the living body mucous membrane 1. Therefore, if the spectral image estimation operation is performed without correcting the spectral image data Gs, it is impossible to obtain spectral operation image data representing a spectral image at a specific wavelength.

Therefore, the value of the spectral image data Gs is corrected to a value obtained by illuminating the living body mucous membrane 1 with white light, in other words, the value of the spectral image data Gs is corrected to a value corresponding to the spectral reflectance of the living body mucous membrane 1. After the value is corrected, the spectral image estimation operation technique, as described above, is applied.

Specifically, when the spectral image data Gs is input to the operation execution unit 26, the value of the spectral image data Gs is corrected by using the value in the red band as a standard, for example. The value of the spectral image data Gs in the red band, which is used as the standard, is not changed, and the value of the spectral image data Gs in the green band is reduced to ½ of the value to obtain corrected spectral image data because the spectral image data Gs in the green band has been received by increasing the light receiving level to twice the light receiving level. Further, the value of the spectral image data Gs in the blue band is reduced to ¼ of the value to obtain corrected spectral image data because the spectral image data Gs in the blue band has been received by increasing a light receiving level to a value four times higher than the light receiving level. The correction processing is performed with reference to the ratio comparison information stored in the ratio comparison information storage unit 22.

Further, a specific wavelength that is effective in diagnosing the living body mucous membrane 1 is specified by the specific wavelength specification switch 28. The specific wavelength is a wavelength, such as a wavelength at which the reflectance of hemoglobin becomes particularly high, for example. When information representing the specified specific wavelength is input to the operation execution unit 26, the operation execution unit 26 obtains spectral reflection estimation matrix data that is used to obtain a ratio between the spectral reflectances at the specified specific wavelengths from the spectral reflection estimation matrix data that has been stored in the matrix data storage unit 24 in advance. Specifically, the operation execution unit 26 obtains the spectral reflection estimation matrix data that is used to obtain a ratio between the intensities of spectral reflection light at specific wavelengths.

Then, the operation execution unit 26 obtains image data representing the intensity of spectral reflection light at the specific wavelength by performing a spectral image estimation operation using the corrected spectral image data and the spectral reflection estimation matrix data corresponding to the specific wavelength. The image data representing the intensity of spectral reflection light at the specific wavelength is spectral operation image data Ge representing a spectral image at each of the specific wavelengths.

The spectral measurement operation image data Gs obtained through the spectral mosaic filter 16 is data representing the intensity of reflection light in a red band, which is a wide band, and the intensity of reflection light in a green band, which is a wide band, and the intensity of reflection light in a blue band, which is a wide band. The reflection light in the red band is light reflected by the living body mucous membrane 1 and transmitted through a red-band-pass filter portion 16R of the spectral mosaic filter 16. The reflection light in the green band is light reflected by the living body mucous membrane 1 and transmitted through a green-band-pass filter portion 16G of the spectral mosaic filter 16. The reflection light in the blue band is light reflected by the living body mucous membrane 1 and transmitted through a blue-band-pass filter portion 16B of the spectral mosaic filter 16. Meanwhile, the spectral measurement operation image data obtained by the operation is data representing the intensity of reflection light, reflected by the living body mucous membrane 1, at a specific wavelength, in other words, in a specific narrow wavelength band.

Specifically, as illustrated in FIG. 7A, the red-band-pass filter portion 16R has a wide-band transmission characteristic Fr. The wide-band spectral transmission characteristic Fr is a characteristic that light in the red band Er is transmitted. The green-band-pass filter portion 16G has a wide-band spectral transmission characteristic Fg. The wide-band spectral transmission characteristic Fg is a characteristic that light in the green band Eg is transmitted. The blue-band-pass filter portion 16B has a wide-band spectral transmission characteristic Fb. The wide-band spectral transmission characteristic Fb is a characteristic that light in the blue band Eb is transmitted. However, if a spectral image estimation operation is performed using the spectral measurement operation image data Ge obtained by receiving light at the imaging unit 12 through each of the band-pass filter portions, it is possible to estimate the value of the intensity of reflection light reflected by the living body mucous membrane 1 in an arbitrary wavelength band $\lambda1, \lambda2, \lambda3, \ldots$, which is narrower than the wide wavelength band, as illustrated in FIG. 7B. In FIG. 7B, a broken line K1' represents a distribution of the intensity of reflection light in the entire wavelength range of visible light. The reflection light is light reflected by the living body mucous membrane 1, and the intensity of the reflection light is an intensity that can be estimated by performing the spectral image estimation operation.

Next, the spectral operation image data Ge, representing a spectral image at the specific wavelength, is input to the image synthesis unit 34 of the diagnostic spectral image production means 30. The image synthesis unit 34 produces a spectral image Gg for diagnosis using the input spectral operation image data Ge and the spectral image data Gs that has been input in advance.

For example, image data Gg for diagnosis that represents a spectral image for diagnosis is produced by synthesizing a spectral image that is produced based on the spectral operation image data Ge, and that corresponds to at least one kind of the specific wavelengths, with an ordinary image that is produced based on the spectral image data Gs. Then, the produced image data Gg for diagnosis is sent to the display monitor 82. Alternatively, image data Gg for diagnosis that represents a spectral image for diagnosis is produced by synthesizing spectral images that are produced based on the spectral operation image data Ge, and that correspond to the two or three kinds of specific wavelengths, which are different from each other. Then, the produced image data Gg for diagnosis is sent to the display monitor 82.

When the image data for diagnosis is input to the display monitor 82, a spectral image for diagnosis represented by the image data for diagnosis is displayed.

When an ordinary image and a spectral image are simultaneously displayed on the display monitor 82, it is possible to display them so that the ordinary image, which is used in ordinary observations, and the spectral image, in which reflection light at a specific wavelength band representing blood is enhanced, are compared with each other. Therefore, doctors can observe very thin blood vessels or the like, which cannot be observed when only the ordinary image is displayed. Hence, this method is very effective in diagnosing living body tissue.

The kind of the diagnostic image displayed on the display monitor 82 is determined by switching the image synthesis selection switch 32.

Figure 8:
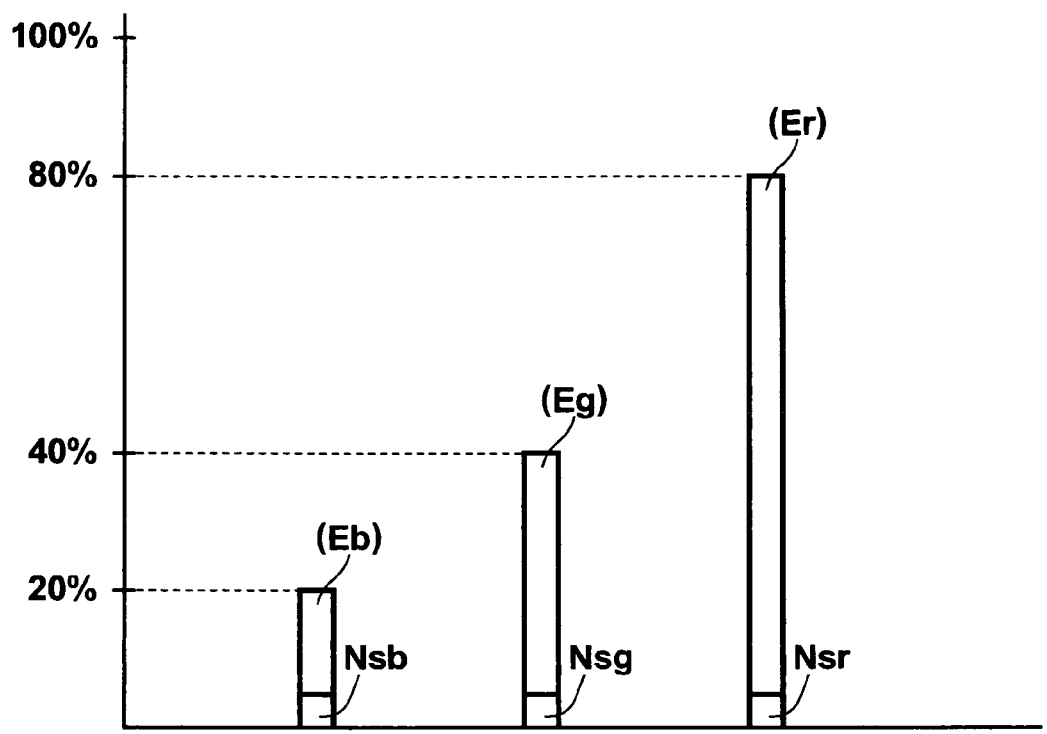
FIG. 8 is a diagram illustrating a ratio of constant noise in the light receiving level at the imaging unit that has received reflection light, reflected by a living body mucous membrane by illumination with white light.
Figure 9:
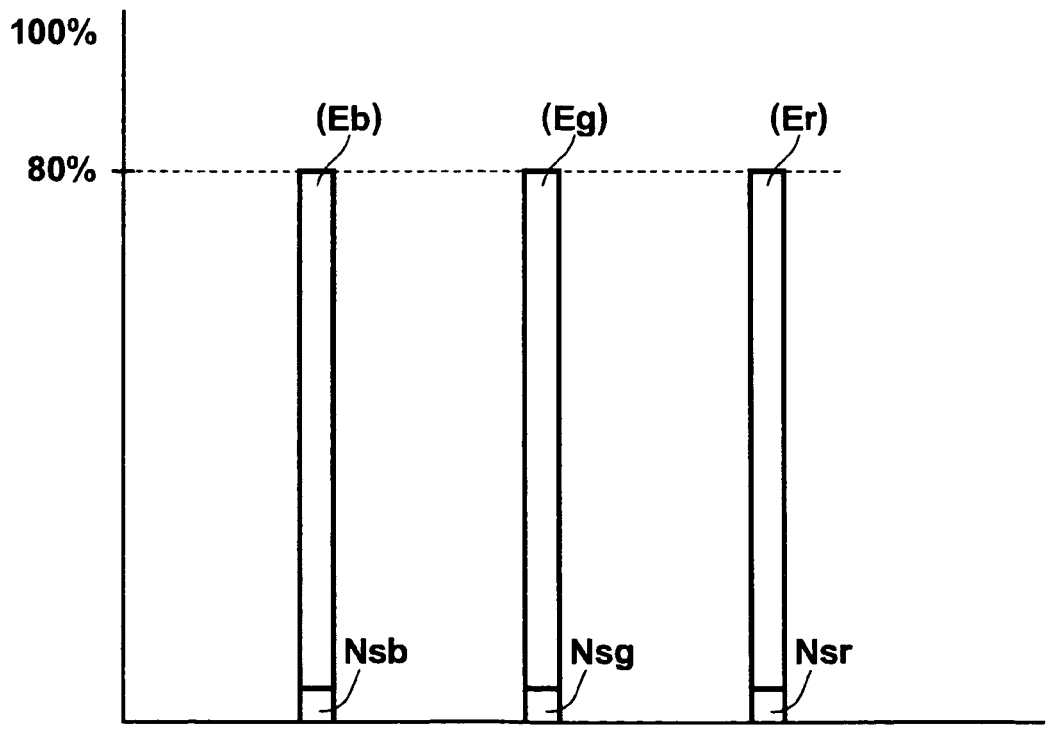
FIG. 9 is a diagram illustrating a ratio of constant noise in the light receiving level at the imaging unit, which has received reflection light reflected by the living body mucous membrane.

Here, the action for reducing a noise component included in the image data for diagnosis by setting the ratio between the light receiving levels with respect to the ratio between the spectral reflectances by the spectral image obtainment means 10 and by performing correction in a spectral image estimation operation by the spectral image data operation means 20 will be described. FIG. 8 is a diagram illustrating a ratio of constant noise in the light receiving level at the imaging unit that has received reflection light reflected by a living body mucous membrane by illumination of the living body mucous membrane with white light. FIG. 9 is a diagram illustrating a ratio of constant noise in the light receiving level at the imaging unit that has received reflection light reflected by the living body mucous membrane. FIG. 10 is a diagram illustrating a ratio of constant noise in a corrected light receiving level.

In each of FIGS. 8, 9 and 10, the vertical axis represents light receiving levels. Further, a light receiving level in the blue band, a light receiving level in the green band and a light receiving level in the red band are illustrated side by side in the direction of the horizontal axis.

If the illumination light projected onto the living body mucous membrane 1 in the spectral image obtainment means 10 is white light, when the reflection light that is reflected by the living body mucous membrane 1 and separated into the wavelength bands is received at the imaging unit 12, the light receiving level in each of the red band Er, the green band Eg and the blue band Eb at the imaging unit 12 is a light receiving level corresponding to the spectral reflectance (please refer to FIG. 4) in the reflection area of the reflection light on the living body mucous membrane 1, as illustrated in FIG. 8. Specifically, if the light receiving level in the red band Er at the imaging unit 12 is 80%, the light receiving level in the green band Eg is 40%, and the light receiving level in the blue band Eb is 20%.

Further, image signals obtained by the imaging unit 12 by receiving light includes a constant noise component Ns, such as a constant noise component Ns caused by dark electric current, for example. The magnitude of the generated constant noise component Ns is not proportional to the intensity of light received by the imaging unit 12. The amount of the generated constant noise component Ns is constant with respect to the maximum light receiving level regardless of the intensity of the received light. If the generation amount of the constant noise component Ns is 1% of the maximum light receiving level, constant noise component Nsr included in spectral image data representing the intensity of reflection light in the red band Er in the obtained spectral image data is 1.25% (1.25%=1%/80%). Similarly, constant noise component Nsg included in spectral image data representing the intensity of reflection light in the green band Eg in the obtained spectral image data is 2.5% (2.5%=1%/40%). Similarly, constant noise component Nsb included in spectral image data representing the intensity of reflection light in the blue band Eb in the obtained spectral image data is 5% (5%=1%/20%).

Therefore, the image for diagnosis that is produced using the spectral image data also includes constant noise component of 1.25% in the red band, constant noise component of 2.5% in the green band and constant noise component of 5% in the blue band.

In contrast, in the present embodiment, as the illumination light with which the living body mucous membrane 1 is illuminated by the spectral image obtainment means 10, illumination light of which the intensity of light in the green band or the blue band is increased relative to the intensity of light in the red band is adopted. When the illumination light is reflected by the living body mucous membrane 1 by illuminating the living body mucous membrane 1 and the reflection light is separated into different wavelength bands and received by the imaging unit 12, the light receiving level in each of the wavelength bands is approximately 80%, as illustrated in FIG. 9. In this case, if the constant noise component Ns, which is not proportional to the intensity of light received by the imaging unit 12, is generated at 1% of the maximum light receiving level in a manner similar to the aforementioned case, the ratio of the constant noise component included in the obtained spectral image data is 1.25% (1.25%=1%/80%) in each of the red band Er, the green band Eg and the blue band Eb.

The ratio of the constant noise included in the spectral image data is not changed even if the value of the spectral image data is corrected by performing a spectral image estimation operation by the operation execution unit 26. For example, even if the value of the spectral image data in the green band Eg that has been received by increasing the light receiving level to twice the light receiving level is reduced to ½ of the value, the ratio of the constant noise included in the spectral image data in the green band Eg is not changed, as illustrated in FIG. 10. Further, even if the value of the spectral image data in the blue band Eb that has been received by increasing the light receiving level to a level four times higher than the light receiving level is reduced to ¼ of the value, the ratio of the constant noise included in the spectral image data in the blue band Eb is not changed. Specifically, the ratio of the constant noise included in the corrected spectral image data is 1.25% in each of the red band Er, the green band Eg and the blue band Eb.

Therefore, when spectral image data is obtained by adopting illumination light in which the intensity of light in a green band and/or a blue band is increased relative to the intensity of light in a red band, it is possible to reduce the ratio of a constant noise component included in the obtained spectral image data than the ratio of a constant noise component included in spectral image data obtained by adopting white light as the illumination light. Accordingly, it is possible to suppress deterioration in the quality of the spectral image for diagnosis.

Regarding the spectral image estimation operation performed by the operation execution unit 26, a case in which the value of the spectral image data obtained by the spectral image obtainment means 10 is corrected has been described. However, it is not necessary that correction is performed in such a manner. The correction amount may be allocated by correcting a coefficient or coefficients of the spectral reflection estimation matrix data.

Specifically, the operation may be performed in any methods as long as a spectral image estimation operation is substantially performed so that the value of the spectral image data obtained by causing the ratio of the intensity of illumination light in a short wavelength band with respect to the intensity of the illumination light in a long wavelength band to be greater is corrected to the value of spectral image data obtained when light is received by the imaging unit 12 without causing the ratio to increase.

Further, the electronic endoscopic apparatus 100 may include a light intensity ratio detection means 110. The light intensity ratio detection means 110 detects the ratio of the intensity of illumination light Le in a short wavelength band with respect to the intensity of the illumination light Le in a long wavelength band. The ratio between the intensities of the illumination light Le corresponds to ratio comparison information represented by the ratio between the light receiving levels with respect to the ratio between the spectral reflectances. Further, the spectral image data operation means 20 may execute the spectral image estimation operation using the ratio comparison information that is input by the light intensity ratio detection means 110 and stored in the ratio comparison information storage unit 22.

The light intensity ratio detection means 110 includes a half mirror 112r for red light, a red light intensity detection unit 114r, a half mirror 112g for green light, a green light intensity detection unit 114g, a half mirror 112b for blue light and a blue light intensity detection unit 114b. The half mirror 112r for red light is placed between the red light source 60R and the condensing lens 62. The half mirror 112r for red light transmits a part of collimated red light emitted from the red light source 60R and reflects the remaining red light. The red light intensity detection unit 114r detects the intensity of light reflected by the half mirror 112r for red light. The half mirror 112g for green light is placed between the green light source 60G and the condensing lens 62. The half mirror 112g for green light transmits a part of collimated green light emitted from the green light source 60G and reflects the remaining green light. The green light intensity detection unit 114g detects the intensity of light reflected by the half mirror 112g for green light. The half mirror 112b for blue light is placed between the blue light source 60B and the condensing lens 62. The half mirror 112b for blue light transmits a part of collimated blue light emitted from the light source 60B for blue light and reflects the remaining blue light. The blue light intensity detection unit 114b detects the intensity of light reflected by the half mirror 112b for blue light.

The light intensity ratio detection means 110 further includes a ratio comparison information obtainment unit 116. The ratio comparison information obtainment unit 116 receives data representing the intensity of light in each wavelength band, which has been reflected by each of the half mirror 112r for red light, the half mirror 112g for green light and the half mirror 112b for blue light and detected by the red light intensity detection unit 114r, the green light intensity detection unit 114g and the blue light intensity detection unit, respectively. Further, the ratio comparison information obtainment unit 116 detects the ratio comparison information represented by the ratio of the intensity of the illumination light Le in the green band with respect to the intensity of the illumination light Le in the red band and the ratio of the intensity of the illumination light Le in the blue band with respect to the intensity of the illumination light Le in the red band. Then, the ratio comparison information obtainment unit 116 outputs the detection result to the ratio comparison information storage unit 22.

Since the light intensity ratio detection means 110 is used, it is possible to perform correction in the spectral image estimation operation without inputting ratio comparison information in advance. Further, even if the intensity of one of the red light, the green light and the blue light, which are emitted from the light sources 60R, 60G and 60B, respectively, fluctuates, the spectral image estimation operation can be performed in such a manner that the correction amount in the operation is adjusted in real time based on the fluctuation amount.

The operation by each of the spectral image obtainment means 10, the spectral image data operation means 20, the diagnostic spectral image production means 30, the light intensity ratio detection means 110 and the like and the timing of each of the operations are controlled by the controller 80. The operation by the spectral image obtainment means 10 is obtainment of spectral image data Gs. The operation by the spectral image data operation means 20 is execution of the spectral image estimation operation. The operation by the diagnostic spectral image production means 30 is production of spectral image data for diagnosis. The operation by the light intensity ratio detection means 110 is detection of ratio comparison information.

When the spectral image obtainment means 10 adopts white light, which has constant intensity through the entire wavelength band of visible light, as the illumination light, it is possible to achieve an effect similar to that described above by applying a spectral mosaic filter 16' instead of the spectral mosaic filter 16, as illustrated in FIG. 2. The spectral mosaic filter 16' is a filter in which the transmittance of a green-band-pass filter portion 16G' and the transmittance of a blue-band-pass filter portion 16B' are greater than the transmittance of a red-band-pass filter portion 16R'. The red-band-pass filter portion 16R' is a portion that transmits reflection light in a long wavelength band. The green-band-pass filter portion 16G' and the blue-band-pass filter portion 16B' are portions that transmit reflection light in a short wavelength band.

Specifically, if the illumination light is the white light and if the spectral transmittance of the red-band-pass filter portion 16R' is 20%, the spectral transmittance of the green-band-pass filter portion 16G' is 40% and the spectral transmittance of the blue-band-pass filter portion 16B' is 80%, it is possible to receive light at the imaging unit 12 at the same light receiving level, for example at 80%, in each of the red band Er, the green band Eg and the blue band Eb. Specifically, it is possible to receive light at the imaging unit 12 at the same light receiving level by causing the ratio of the transmittance of a spectral filter portion that transmits reflection light in the red band, which is a long wavelength band, with respect to the transmittance of a spectral filter portion that transmits reflection light in a short wavelength band, such as the green band and the blue band, to be substantially the same as the ratio of the spectral reflectance in a short wavelength band in the reflection area of the reflection light on the living body mucous membrane with respect to the spectral reflectance in the long wavelength band in the reflection area of the reflection light on the living body mucous membrane. Accordingly, an effect similar to the effect as described above can be achieved.

The spectral mosaic filter 16' is used to project illumination light in such a manner that the ratio Ht (Ht=20%/40%=1/2) of the transmittance (20%) of a spectral filter portion that transmits reflection light in a red band, which is a long wavelength band, in the mosaic filter 16' with respect to the transmittance (40%) of a spectral filter portion that transmits reflection light in a green band, which is a short wavelength band, in the mosaic filter 16' is substantially the same as the ratio Hk (Hk=1%/2%=1/2) of the spectral reflectance in the green band, that is a short wavelength band, in the reflection area of the reflection light on the living body mucous membrane 1 with respect to the spectral reflectance in the red band, which is a long wavelength band, in the reflection area of the reflection light on the living body mucous membrane 1.

Further, the spectral mosaic filter 16' is used to project illumination light in such a manner that the ratio Ht (Ht=20%/80%=1/4) of the transmittance (20%) of a spectral filter portion that transmits reflection light in a red band, which is a long wavelength band, in the mosaic filter 16' with respect to the transmittance (80%) of a spectral filter portion that transmits reflection light in a blue band, which is a short wavelength band, in the mosaic filter 16' is substantially the same as the ratio Hk (Hk=0.5%/2%=1/4) of spectral reflectance in the blue band, which is a short wavelength band, in the reflection area of the reflection light on the living body mucous membrane 1 with respect to spectral reflectance in the red band, which is a long wavelength band, in the reflection area of the reflection light on the living body mucous membrane 1.

In such a case, ratio comparison information represented by the ratio of the transmittance of the green-band-pass filter portion 16G' with respect the transmittance of the red-band-pass filter portion 16R' and the ratio of the transmittance of the blue-band-pass filter portion 16B' with respect the transmittance of the red-band-pass filter portion 16R' is stored in the comparison information storage unit 22, and the spectral image estimation operation is performed.

Further, an effect similar to that of the above embodiment, namely an effect of causing the light receiving level in each of the red band, the green band and the blue band at the imaging unit 12 to be the same level, such as 70% and 90%, may be achieved by combining processing for changing the spectral transmittance distribution of the illumination light propagation optical system 64, processing for changing the spectral transmittance distribution of the object lens 18, processing for changing the spectral transmittance distribution of each of the spectral band-pass filter portions in the spectral mosaic filter 16, processing for changing the spectral intensity distribution of the light source 60 and the like.

Further, in the above descriptions, a case in which the light receiving level in each of the red band, the green band and the blue band is caused to be substantially the same has been explained. However, an effect similar the effect achieved in the above embodiment can be achieved by setting the spectral transmission distribution and/or the spectral intensity distribution in each of the units so that the light receiving level in the short wavelength band is increased without decreasing the light receiving level in the long wavelength band. For example, a difference between the light receiving levels may be caused to be within ±10% of each of the light receiving levels. Alternatively, the light receiving level in each of the wavelength bands at the light receiving means may be caused to be higher than or equal to 50% of the maximum light receiving level, or preferably higher than or equal to 80% of the maximum light receiving level.

When the distribution is set, as described above, ratio comparison information is updated based the setting of the spectral image obtainment means 10. Specifically, the ratio comparison information is changed based on the setting at the spectral image obtainment means 10. The ratio comparison information is information representing the ratio of the light receiving level of reflection light in a short wavelength band, reflected by the living body mucous membrane 1, at the light receiving means with respect to the light receiving level of the reflection light in a long wavelength band at the light receiving means with respect to the ratio of spectral reflectance in the short wavelength band at the living body mucous membrane 1 with respect to spectral reflectance in the long wavelength band at the living body mucous membrane 1. Then, the ratio comparison information is stored in the ratio comparison information storage unit 22.

Each of the wavelength bands that are different from each other are not limited to the red band, the green band and the blue band, and other kinds of wavelength bands may be utilized. Two or four kinds of wavelength bands or more bands that are different from each other, such as wavelength bands of cyan, magenta, yellow and green (G, Cy, Mg and Ye), which are complementary colors, may be used, for example, to produce a spectral image for diagnosis. When the spectral image for diagnosis is produced in such a manner, it is possible to achieve an effect similar to that achieved in the above embodiment.

What is claimed is:

1. An electronic endoscopic apparatus comprising:
   a spectral image obtainment module of a plane-simultaneous method including a light receiving unit for receiving reflection light in each of wavelength bands that are different from each other, and into which reflection light of illumination light, reflected by a living body mucous membrane by illumination with the illumination light, is separated, the spectral image obtainment module obtaining spectral image data representing a spectral image of the living body mucous membrane;
   a spectral image data operation module configured for obtaining spectral operation image data representing a spectral image of the living body mucous membrane at a specific wavelength by performing a spectral image estimation operation based on the spectral operation image data and spectral reflection estimation matrix data that has been input and stored in advance; and
   a diagnostic spectral image production module configured for producing, based on the spectral operation image data, a spectral image of the living body mucous membrane for diagnosis, wherein the spectral image obtainment module receives the reflection light by causing ratio Hj (Hj=Js/Jp) of light receiving level Js at the light receiving unit that has received reflection light in a short wavelength band on the short wavelength side of a long wavelength band, the long wavelength band being the longest wavelength band of the different wavelength bands, with respect to light receiving level Jp at the light receiving unit that has received reflection light in the long wavelength band to be greater than ratio Hk (Hk=Ks/Kp) of spectral reflectance Ks in the short wavelength band in a reflection area of the reflection light on the living body mucous membrane with respect to spectral reflectance Kp in the long wavelength band in the reflection area of the reflection light on the living body mucous membrane (Hj>Hk), and wherein the spectral image data operation module is configured to perform the spectral image estimation operation by correcting the value of the spectral image data that corresponds to the short wavelength band, and that has been obtained by receiving light at the light receiving unit by causing the ratio of the light receiving level in the short wavelength band with respect to the light receiving level in the long wavelength band to be greater, to the value of spectral image data that corresponds to the short wavelength, and that is obtained by receiving light at the light receiving unit without causing the ratio of the light receiving level in the short wavelength band with respect to the light receiving level in the long wavelength band to increase.

2. An electronic endoscopic apparatus, as defined in claim 1, wherein the wavelength bands that are different from each other are a red band, a green band and a blue band.

3. An electronic endoscopic apparatus, as defined in claim 2, wherein the spectral image obtainment module receives the reflection light in such a manner that the light receiving level in each of the different wavelength bands at the light receiving unit is higher than or equal to 50% of a maximum light receiving level.

4. An electronic endoscopic apparatus, as defined in claim 1, wherein the spectral image obtainment module receives the reflection light in such a manner that the light receiving level in each of the different wavelength bands at the light receiving unit is higher than or equal to 50% of a maximum light receiving level.

5. An electronic endoscopic apparatus, as defined in claim 4, wherein the spectral image obtainment module receives the reflection light in such a manner that the light receiving level in the short wavelength band at the light receiving unit is substantially the same as the light receiving level in the long wavelength band at the light receiving unit.

6. An electronic endoscopic apparatus, as defined in claim 4, wherein the spectral image obtainment module includes an illumination module for emitting the illumination light, and wherein the illumination module emits the illumination light in such a manner that ratio Hm of the intensity of light in the long wavelength band at the illumination module with respect to the intensity of light in the short wavelength band at the illumination module is substantially the same as the ratio Hk between the spectral reflectances.

7. An electronic endoscopic apparatus, as defined in claim 4, further comprising:
   a light intensity ratio detection module configured for detecting a ratio of the intensity of the illumination light in the short wavelength band with respect to the intensity of the illumination light in the long wavelength band, wherein the spectral image data operation module performs correction in the spectral image estimation operation using the ratio detected by the light intensity ratio detection module.

8. An electronic endoscopic apparatus, as defined in claim 4, wherein the spectral image obtainment module includes a spectral mosaic filter for separating the reflection light reflected by the living body mucous membrane into wavelength bands different from each other, and wherein the spectral mosaic filter is a filter in which ratio Ht of the transmittance of a spectral filter portion that transmits reflection light in the long wavelength band with respect to the transmittance of a spectral filter portion that transmits reflection light in the short wavelength band is substantially the same as the ratio Hk between the spectral reflectances.

9. An electronic endoscopic apparatus, as defined in claim 1, wherein the spectral image obtainment module receives the reflection light in such a manner that the light receiving level in the short wavelength band at the light receiving unit is substantially the same as the light receiving level in the long wavelength band at the light receiving unit.

10. An electronic endoscopic apparatus, as defined in claim 9, further comprising:
  a light intensity ratio detection module configured for detecting a ratio of the intensity of the illumination light in the short wavelength band with respect to the intensity of the illumination light in the long wavelength band, wherein the spectral image data operation module performs correction in the spectral image estimation operation using the ratio detected by the light intensity ratio detection module.

11. An electronic endoscopic apparatus, as defined in claim 9, wherein the spectral image obtainment module includes a spectral mosaic filter for separating the reflection light reflected by the living body mucous membrane into wavelength bands different from each other, and wherein the spectral mosaic filter is a filter in which ratio Ht of the transmittance of a spectral filter portion that transmits reflection light in the long wavelength band with respect to the transmittance of a spectral filter portion that transmits reflection light in the short wavelength band is substantially the same as the ratio Hk between the spectral reflectances.

12. An electronic endoscopic apparatus, as defined in claim 1, wherein the spectral image obtainment module includes an illumination module for emitting the illumination light, and wherein the illumination module emits the illumination light in such a manner that ratio Hm of the intensity of light in the long wavelength band at the illumination module with respect to the intensity of light in the short wavelength band at the illumination module is substantially the same as the ratio Hk between the spectral reflectances.

13. An electronic endoscopic apparatus, as defined in claim 12, wherein the illumination module includes individual light sources that emit light corresponding to the respective wavelength bands, which are different from each other.

14. An electronic endoscopic apparatus, as defined in claim 12, further comprising:
  a light intensity ratio detection module configured for detecting a ratio of the intensity of the illumination light in the short wavelength band with respect to the intensity of the illumination light in the long wavelength band, wherein the spectral image data operation module performs correction in the spectral image estimation operation using the ratio detected by the light intensity ratio detection module.

15. An electronic endoscopic apparatus, as defined in claim 1, further comprising:
  a light intensity ratio detection module configured for detecting a ratio of the intensity of the illumination light in the short wavelength band with respect to the intensity of the illumination light in the long wavelength band, wherein the spectral image data operation module performs correction in the spectral image estimation operation using the ratio detected by the light intensity ratio detection module.

16. An electronic endoscopic apparatus, as defined in claim 1, wherein the spectral image obtainment module includes a spectral mosaic filter for separating the reflection light, reflected by the living body mucous membrane, into wavelength bands different from each other, and wherein the spectral mosaic filter is a filter in which ratio Ht of the transmittance of a spectral filter portion that transmits reflection light in the long wavelength band with respect to the transmittance of a spectral filter portion that transmits reflection light in the short wavelength band is substantially the same as the ratio Hk between the spectral reflectances.

* * * * *